(12) United States Patent
Kopkalli et al.

(10) Patent No.: US 8,067,649 B2
(45) Date of Patent: *Nov. 29, 2011

(54) METHOD FOR PRODUCING FLUORINATED ORGANIC COMPOUNDS

(75) Inventors: Haluk Kopkalli, Staten Island, NY (US); Yuon Chiu, Denville, NJ (US); Hsueh Sung Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 136 days.

This patent is subject to a terminal disclaimer.

(21) Appl. No.: 12/466,271

(22) Filed: May 14, 2009

(65) Prior Publication Data

US 2011/0207974 A9    Aug. 25, 2011

Related U.S. Application Data

(63) Continuation-in-part of application No. 11/619,592, filed on Jan. 3, 2007.

(60) Provisional application No. 61/053,647, filed on May 15, 2008.

(51) Int. Cl.
*C07C 17/25* (2006.01)

(52) U.S. Cl. ........ 570/155; 570/135; 570/157; 570/164; 570/179; 570/188

(58) Field of Classification Search .......................... None
See application file for complete search history.

(56) References Cited

U.S. PATENT DOCUMENTS

| 2,931,840 | A | 4/1960 | Marquis |
| 4,900,874 | A | 2/1990 | Ihara et al. |
| 5,162,594 | A | 11/1992 | Krespan |
| 2006/0030744 | A1 | 2/2006 | Mukhopadhyay et al. |
| 2007/0179324 | A1 | 8/2007 | Van Der Puy et al. |
| 2007/0197841 | A1 | 8/2007 | Mukhopadhyay et al. |
| 2007/0197842 | A1* | 8/2007 | Mukhopadhyay et al. ... 570/155 |

FOREIGN PATENT DOCUMENTS

| WO | WO2005108334 | 11/2005 |
| WO | WO2007079431 | 7/2007 |

OTHER PUBLICATIONS

R. Eric Banks et al., Preparation of 2,3,3,3-tetrafluoropropene From Trifluoroacetylacetone and Sulphur Tetrafluoride, Journal of Fluorine Chemistry, vol. 82 (1997), pp. 171-174. US.

Knunyants, I.L., et al.: "Reactions of Fluoro Olefins. XIII. Catalytic Hydrogenation of Perfluoro Olefins.": Izvestiya Akademii Nauk SSSR, Seriya Khimicheskaya 1412-18 CODEN: IASKA6; ISSN: 0002-3353, 1960, XP002548816—pp. 1313, 1316.

* cited by examiner

*Primary Examiner* — Sudhakar Katakam
(74) *Attorney, Agent, or Firm* — Bruce Bradford

(57) ABSTRACT

Disclosed is a process for producing tetrafluoropropene comprising: (a) catalytically fluorinating at least one tetrafluoropropene in a first reactor to produce HCFO-1233xf; (b) reacting said HCFO-1233xf with hydrogen fluoride in a second reactor to produce HCFC-244bb; (c) recycling at least a portion of said HCFC-244bb back to said first reactor as recycled HCFC-244bb; and (d) catalytically dehydrochlorinating said recycled HCFC-244bb in said first reactor to produce HFO-1234yf.

20 Claims, 2 Drawing Sheets

Block Flow Diagram for Production of HFO-1234yf from TCP

R-1: TCP + HF → 1233xf + HCl (fluorination catalyst)
    244bb → 1234yf + HCl (dehydrochlorination catalyst)

R-2: 1233xf + HF → 244bb

Process Flow Diagram for Production of HFO-1234yf from TCP

METHOD FOR PRODUCING FLUORINATED ORGANIC COMPOUNDS

RELATED APPLICATIONS

The present application is related to and claims the priority benefit of U.S. Provisional Patent Application No. 61/053,647, which was filed on May 15, 2008, and which is incorporated herein by reference. The present application is also a continuation-in-part of U.S. patent application Ser. No. 11/619,592, filed Jan. 3, 2007.

BACKGROUND OF INVENTION (1) Field of Invention

This invention relates to novel methods for preparing fluorinated organic compounds, and more particularly to methods of producing fluorinated olefins.

(2) Description of Related Art

Hydrofluorocarbons (HFC's), in particular hydrofluoroalkenes such as tetrafluoropropenes (including 2,3,3,3-tetrafluoro-1-propene (HFO-1234yf) and 1,3,3,3-tetrafluoro-1-propene (HFO-1234ze)) have been disclosed to be effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFCs do not contain chlorine and thus pose no threat to the ozone layer.

Several methods of preparing hydrofluoroalkenes are known. For example, U.S. Pat. No. 4,900,874 (Ihara et al.) describes a method of making fluorine containing olefins by contacting hydrogen gas with fluorinated alcohols. Although this appears to be a relatively high-yield process, for commercial scale production the handling of hydrogen gas at high temperature raises difficult safety-related questions. Also, the cost of producing hydrogen gas, such as building an on-site hydrogen plant, can be in many situations prohibitive.

U.S. Pat. No. 2,931,840 (Marquis) describes a method of making fluorine containing olefins by pyrolysis of methyl chloride and tetrafluoroethylene or chlorodifluoromethane. This process is a relatively low yield process and a very large percentage of the organic starting material is converted in this process to unwanted and/or unimportant byproducts.

The preparation of HFO-1234yf from trifluoroacetylacetone and sulfur tetrafluoride has been described. See Banks, et al., Journal of Fluorine Chemistry, Vol. 82, Iss. 2, p. 171-174 (1997). Also, U.S. Pat. No. 5,162,594 (Krespan) discloses a process wherein tetrafluoroethylene is reacted with another fluorinated ethylene in the liquid phase to produce a polyfluoroolefin product.

Multi-step methods of producing HFO-1234yf and HFO-1234ze are described in US 2007/0197842 (Mukhopadhyay et al.). More particularly, this publication describes a method for producing HFO-1234yf that involves converting tetrachloropropenes into an intermediate trifluoropropene, such as 2-chloro-3,3,3,-trifluoro-1-propene (HCFO-1233xf), which can subsequently be converted into 2-chloro-1,1,1,2-tetrafluoropropane (HCFC-244bb), which can subsequently be converted into HFO-1234yf. Such a method involves a series of reactors.

There remains a need for a method for producing HFO-1234yf that is more efficient and economically practical. This invention satisfies these needs among others.

SUMMARY OF THE INVENTION

Applicants have found a method of producing HFO-1234yf from tetrachloropropene (TCP) that involves using a single reactor or reactor system to conduct two different reaction steps contemporaneously, namely fluorination of tetrachloropropene to produce an HFCO-1233xf intermediate and dehydrochlorination of HCFC-244bb to produce HFO-1234yf. Compared to conventional three-step processes for the manufacture of HFO-1234yf from TCP via three separate reactors, the present invention reduces the unit operations and processing equipment. This results in a more economical process from an initial capital and operating cost versus conducting the 3-steps sequentially.

Accordingly, an aspect of the invention provides a process for producing tetrafluoropropene comprising: (a) catalytically fluorinating at least one tetrafluoropropene in a first reactor to produce HCFO-1233xf; (b) reacting said HCFO-1233xf with hydrogen fluoride in a second reactor to produce HCFC-244bb; (c) recycling at least a portion of said HCFC-244bb back to said first reactor as recycled HCFC-244bb; and (d) catalytically dehydrochlorinating said recycled HCFC-244bb in said first reactor to produce HFO-1234yf.

According to another aspect of the invention, provided is a process for producing tetrafluoropropene comprising: (a) introducing one or more feed streams into a first reactor containing a fluorination catalyst and a dehydrochlorination catalyst, wherein said feed streams collectively comprise tetrachloropropene, hydrogen fluoride, and HCFC-244bb; (b) contacting said one or more feed streams with said fluorination catalyst and said dehydrochlorination catalyst to produce a first intermediate product stream comprising HCFO-1233xf and HFO-1234yf; (c) converting at least a portion of said HCFO-1233xf into HCFC-244bb in a second reactor to produce a second intermediate product stream; (d) separating said intermediate product stream into a product stream rich in HFO-1234yf and a recycle product stream rich in HCFC-244bb; and (e) introducing said recycle product stream into said first reactor as said one or more feed streams.

DETAILED DESCRIPTION OF PREFERRED EMBODIMENTS OF THE INVENTION

Figure 1:
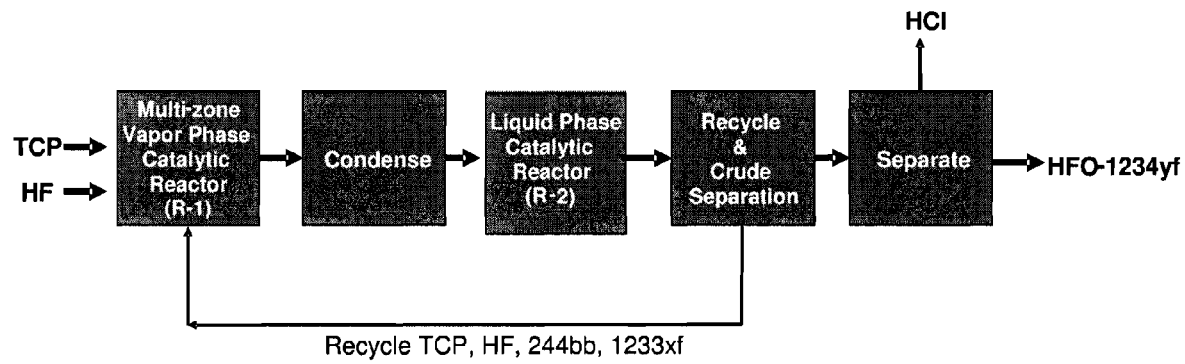
FIG. 1 is a block flow diagram showing the production of HFO-1234yf from TCP according to a preferred embodiment of the invention.

Applicants have discovered an integrated method for producing fluorinated organic compounds, including hydrofluoropropenes such as HFO-1234yf, which preferably comprises converting at least one compound of formula $C(X)_2=CClC(X)_3$, and more preferably at least one compound of Formula (I):

$$CHX=CClC(X)_3 \qquad (I)$$

into at least one compound of Formula (II):

$$CF_3CF=CHZ \qquad (II)$$

where each X is independently H or Cl, and Z is independently H or Cl. Preferably, the compound of Formula (II) is $CF_3CF=CH_2$.

In a preferred aspect of the present invention, the method comprises: (a) reacting, preferably fluorinating, and even more preferably fluorinating in the presence of HF, a compound of Formula (I), preferably a tetrachloropropene, and even more preferably a tetrachloropropene selected from the group consisting of $CH_2=CClCCl_3$, $CCl_2=CClCH_2Cl$, $CHCl=CClCCl_2H$, and combinations of these, in a gas and/or liquid phase reaction in the presence of at least a first catalyst to produce at least one compound of formula $C(X)_2=CClCF_3$, and preferably of Formula (IA):

$$CHX=CClCF_3 \qquad (IA)$$

wherein X is H or Cl, such as a monochloro-trifluoro-propene, preferably HCFO-1233xf; (b) reacting at least one compound produced from step (a), preferably a compound of Formula (IA), in a gas and/or liquid phase and preferably in the presence of at least a catalyst, preferably a second catalyst which is different than the first catalyst, to produce at least one compound of formula $C(X)_3CClYC(X)_3$, wherein X and Y are independently H, F, or Cl, and preferably of Formula (IB):

$$CH_2XCClFCF_3 \qquad (IB)$$

wherein X is H or Cl, such as HCFC-244bb; and (c) reacting said compound of Formula (IB), in a gas and/or liquid phase, to produce at least one compound of Formula (II), preferably HFO-1234yf; wherein steps (a) and (c) are performed in a single reactor or reactor zone. In certain embodiments steps (a) and (c) may be performed in a hydrofluorination zone and a dehydrochlorination zone, respectively, of a single reactor. The reaction zones are preferably separated by a physical barrier. For example, a single reactor may comprise a shell and tube, whereby step (a) is performed on the shell side of the reactor, and step (c) is performed on the tube side of the reactor, or vice-a-versa. Each of the preferred reaction steps is described in detail below, with the headings being used for convenience but not necessarily by way of limitation.

A. Fluorination of the Compound of Formula (I):

One preferred reaction step in accordance with the present invention may be described by those reactions in which the compound of Formula (I) is fluorinated to produce a compound of Formula (IA). In certain preferred embodiments, the converting step involves reacting said compound(s) by fluorinating said compound(s) with a fluorinating agent, preferably selected from HF, $F_2$, and FCl, and more preferably HF, in a gas phase, to produce hydrochlorofluoroolefin that is at least trifluorinated, such as HCFO-1233xf. Preferably this is a gas phase reaction that is at least partially catalyzed.

The preferred fluorination of the compound of Formula (I) is preferably carried out under conditions effective to provide a Formula (I) conversion of at least about 50%, more preferably at least about 75%, and even more preferably at least about 90%. In certain preferred embodiments the conversion is at least about 95%, and more preferably at least about 97%. Further in certain preferred embodiments, the conversion of the compound of Formula (I) comprises reacting such compound under conditions effective to produce at least one compound of Formula (IA), such as monochlorotrifluoropropene (preferably HCFO-1233xf)) at a selectivity of at least about 50%, more preferably at least about 70%, more preferably at least about 80%, and even more preferably at least about 90%, with selectivities of about 95% or greater being achieved in certain embodiments.

In general, it is possible that the fluorination reaction step can be carried out in the liquid phase or in the gas phase, or in a combination of gas and liquid phases, and it is contemplated that the reaction can be carried out batch wise, continuous, or a combination of these.

In preferred gas phase fluorination of Formula (I) compounds, the reaction is at least partially a catalyzed reaction, and is preferably carried out on a continuous basis by introducing a stream containing the compound of Formula (I), into one or more reaction vessels, such as a tubular reactor. Particularly preferred reactor systems include single reactor systems using a series of reactors, multistage reactors, or a combination reactor design. For embodiments using a single reactor, the reactor is preferably segregated into alternating beds of fluorination and dehydrochlorination zones or contains a homogeneous mixture of fluorination and dehydrochlorination catalysts.

In certain preferred embodiments, the stream containing the compound of Formula (I), is heated to a temperature of from about 80° C. to about 400° C., more preferably from about 150° C. to about 400° C., and in certain embodiments preferably about 300° C., and introduced into a reaction vessel, which is maintained at the desired temperature, preferably from about 80° C. to about 700° C., more preferably from about 90° C. to about 600° C., even more preferably in certain embodiments from about 400° C. to about 600° C., more preferably from about 450° C. to about 600° C., where it is preferably contacted with catalyst and fluorinating agent, such as HF. As described in more detail below, the exothermic fluorination of the Compound of Formula (I) and the endothermic dehydrochlorination of Formula (IB) are preferably performed in the same reactor. Preferably the exothermic properties of the fluorination are balanced with the endothermic properties of the dehydrochlorination.

Preferably the vessel is comprised of materials which are resistant to corrosion as Hastelloy, Inconel, Monel and/or fluoropolymers linings.

Preferably the vessel contains catalyst, for example a fixed or fluid catalyst bed, packed with a suitable fluorination catalyst, with suitable means to ensure that the reaction mixture is maintained with the desired reaction temperature range.

Thus, it is contemplated that the fluorination reaction step may be preformed using a wide variety of process parameters and process conditions in view of the overall teachings contained herein. However, it is preferred in certain embodiments that this reaction step comprise a gas phase reaction, preferably in the presence of catalyst, and even more preferably a chromium-based catalyst (such as $Cr_2O_3$ catalyst), an iron-based catalyst (such as $FeCl_3$ on carbon (designated herein as $FeCl_3/C$ for convenience), and combinations of these. In preferred embodiments, the catalyst is a combination of the two aforementioned catalysts, where the reaction vessel contains in a first zone the chromium-based catalyst and in a second zone the iron-based catalyst. The temperature of the reaction in the chromium-based catalyst reaction is preferably kept at a temperature of from about 200° C. to about 600° C. and even more preferably from about 250° C. to about 500° C. The temperature of the reaction in the iron-based catalyst reaction zone is preferably kept at a temperature of from about 80° C. to about 300° C. and even more preferably from about 100° C. to about 250° C.

In general it is also contemplated that a wide variety of reaction pressures may be used for the fluorination reaction, depending again on relevant factors such as the specific catalyst being used and the most desired reaction product. The reaction pressure can be, for example, superatmospheric, atmospheric or under vacuum and in certain preferred embodiments is from about 1 to about 200 psia, and in certain embodiments from about 1 to about 120 psia.

In certain embodiments, an inert diluent gas, such as nitrogen, may be used in combination with the other reactor feed(s).

It is contemplated that the amount of catalyst use will vary depending on the particular parameters present in each embodiment.

B. Fluorination of the Compound of Formula I(A):

The compound of Formula (IA), preferably produced as described above, is preferably subject to further fluorination reaction(s) involving a fluorinating agent, preferably selected from HF, $F_2$, and FCl, and more preferably HF, to produce a compound of Formula (IB), preferably HCFC-244bb. Preferably, this is a liquid phase reaction that is at least partially catalyzed. Preferably this reaction is performed in a reactor separate from the reactor used to perform the fluorination of Formula (I) and the dehydrochlorination of Formula (IB).

The fluorination of the compound of Formula (IA) is preferably carried out under conditions effective to provide a Formula (IA) conversion of at least about 40%, more preferably at least about 50%, and even more preferably at least about 60%. Further, in certain preferred embodiments, the conversion of the compound of Formula (IA) comprises reacting such compound under conditions effective to produce at least one monochlorotetrafluoropropane, preferably HCFC-244bb, at a selectivity of at least about 70%, more preferably at least about 80%, and even more preferably at least about 85%, with selectivities of about 90% or greater being achieved in certain embodiments.

In general, it is possible that this fluorination reaction step can be carried out in the liquid phase or in the gas phase, or in a combination of gas and liquid phases, and it is contemplated that the reaction can be carried out batch wise, continuous, or a combination of these.

For embodiments in which the reaction comprises a liquid phase reaction, the reaction can be catalytic or non-catalytic. Preferably, a catalytic process is used. Lewis acid catalyst, such as metal-halide catalysts, including antimony halides, tin halides, thallium halides, iron halides, and combinations of two or more of these, are preferred in certain embodiments. Metal chlorides and metal fluorides are particularly preferred. Examples of particularly preferred catalysts of this type include $SbCl_5$, $SbCl_3$, $SbF_5$, $SnCl_4$, $TiCl_4$, $FeCl_3$ and combinations of two or more of these.

In preferred gas phase fluorination of Formula (IA) compounds, the reaction is at least partially a catalyzed reaction, and is preferably carried out on a continuous basis by introducing a stream containing the compound of Formula (IA) into one or more reaction vessels, such as a tubular reactor. In certain preferred embodiments, the stream containing the compound of Formula (IA) is preheated to a temperature of from about 50° C. to about 400° C., and in certain embodiments preferably about 80° C. In other embodiments, it is preferred that the stream containing the compound of Formula (IA), is preheated to a temperature of from about 150° C. to about 400° C., preferably about 300° C. This steam, preferably after preheating, is then preferably introduced into a reaction vessel (preferably a tube reactor), which is maintained at the desired temperature, preferably from about 50° C. to about 250° C., more preferably from about 50° C. to about 150° C., where it is preferably contacted with catalyst and fluorinating agent, such as HF.

Preferably the vessel is comprised of materials which are resistant to corrosion as Hastelloy, Inconel, Monel and/or fluoropolymers linings.

Preferably the vessel contains catalyst, for example a fixed or fluid catalyst bed, packed with a suitable fluorination catalyst, with suitable means to ensure that the reaction mixture is maintained within about the desired reaction temperature range.

Thus, it is contemplated that the fluorination reaction step may be preformed using a wide variety of process parameters and process conditions in view of the overall teachings contained herein. However, it is preferred in certain embodiments that this reaction step comprises a liquid phase reaction, preferably in the presence of catalyst, and even more preferably an Sb-based catalyst, such as catalyst which is about 50 wt % $SbCl_5$/C. Other catalysts which may be used include: from about 3 to about 6 wt % $FeCl_3$/C; $SbF_5$/C; about 20 wt % $SnCl_4$/C; about 23 wt % $TiCl_4$/C; and activated carbon. Preferably the catalyst comprises $Cl_2$ and HF pre-treated $SbCl_5$/C.

In general it is also contemplated that a wide variety of reaction pressures may be used for the fluorination reaction, depending again on relevant factors such as the specific catalyst being used and the most desired reaction product. The reaction pressure can be, for example, superatmospheric, atmospheric or under vacuum and in certain preferred embodiments is from about 1 to about 200 psia, more preferably in certain embodiments from about 1 to about 120 psia.

It is contemplated that the amount of catalyst used will vary depending on the particular parameters present in each embodiment.

C. Dehydrohalogenation of Formula (IB):

One preferred reaction step in accordance with the present invention may be described by those reactions in which the compound of Formula (IB) is dehydrohalogenated to produce a compound of Formula (II). Preferably, the reaction is performed contemporaneously with the fluorination of the compound of Formula (I) and in the same reactor or reactor system that is used to fluorinate the compound of Formula (I). Preferably, the dehydrohalogenation of Formula (IB) involves a gas phase catalytic reaction. Preferred dehydrochlorination catalysts include carbon- and/or metal-based catalyst, preferably activated carbon, a nickel-based catalyst (such as Ni-mesh) and combinations of these. Other catalysts and catalyst supports may be used, including palladium on carbon, palladium-based catalyst (including palladium on aluminum oxides), and it is expected that many other catalysts may be used depending on the requirements of particular embodiments in view of the teachings contained herein. Of course, two or more any of these catalysts, or other catalysts not named here, may be used in combination.

Preferably in such dehydrofluorination embodiments as described in this section, the conversion of the Formula (IB) compound is at least about 60%, more preferably at least about 75%, and even more preferably at least about 90%. Preferably in such embodiments, the selectivity to compound of Formula (II), preferably HFO-1234yf, is at least about 50%, more preferably at least about 70% and more preferably at least about 80%.

Example

The following prophetic example is a preferred embodiment that is provided to further illustrate certain aspect of the invention.

Figure 2:
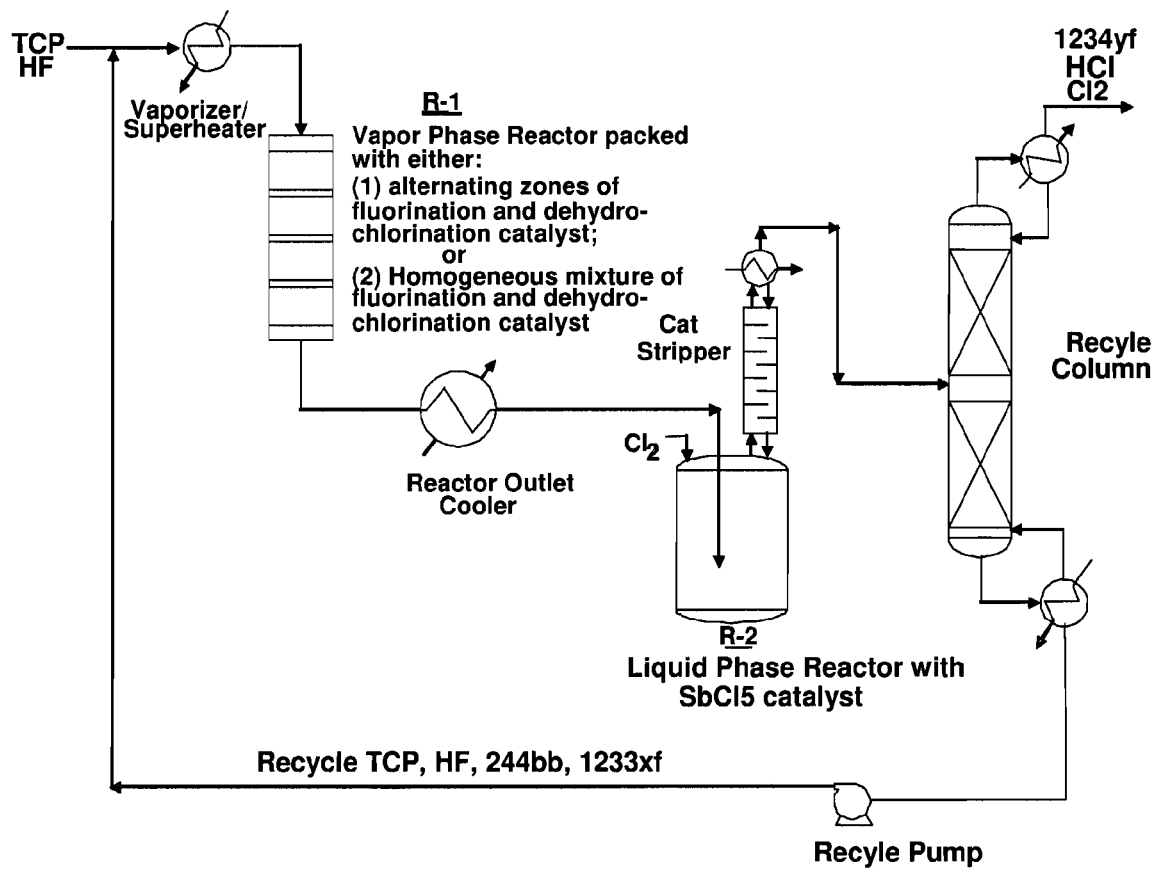
FIG. 2 is a process flow diagram showing a preferred embodiment of the invention.

With reference to FIGS. 1 and 2, shown is an integrated process for the production of HFO-1234yf from tetrachloropropene (TCP) in three reaction steps where the first (exothermic) and third (endothermic) reactions are carried out in a single reactor or reaction zone. The process is summarized as follows:

Step 1: Hydrofluorination of TCP to HCFO-1233xf and dehydrochlorination of intermediate HCFC-244bb (formed in a separate reactor as described below) occur in a single reactor system using a series of reactors or multi-stage reactor, or combination of reactor design, as illustrated on the attached process flowsheet. The reactor is either segregated into alternating beds of fluorination/dehydrochlorination zones or a homogeneous mixture of fluorination catalyst and dehydrochlorination catalyst. The exotherm of the hydrofluorination reaction is used to balance the endotherm of the dehydrochlorination reaction.

Step 2: The reactor effluent containing HCFO-1233xf, HFO-1234yf, HCFC-244bb, HCl and any unreacted TCP and intermediates are cooled and condensed into a liquid and are fed as an intermediate product stream into a liquid phase reactor containing antimony pentachloride catalyst for hydrofluorination of HCFO-1233xf to HCFC-244bb.

Step 3: The combined mixture of HCFO-1233xf, HCFC-244bb, HFO-1234yf and HCl exit the liquid reactor system as a second intermediate product stream and are processed via a catalyst stripper so that most of the unreacted HF and catalyst are refluxed back to the second reactor. If desired, further conversion of HCFO-1233xf may be accomplished in a post-catalysis section comprised of SbCl$_5$/C catalyst fitted to the exit of the catalyst stripper.

Step 4: The effluent from the catalyst stripper is fed to a recycle column, such as a distillation column, to separate the HCFO-1233xf, HCFC-244bb and HF from the HFO-1234yf. The HCFO-1233xf, HCFC-244bb and HF exit the bottom of distillation column and are recycled back to the first reactor.

Step 5: The distillate from the distillation column is fed to additional equipment such as HCl recovery column to separate desired product HFO-1234yf from HCl. Alternatively, the HCl may be scrubbed out and desired product HFO-1234yf may be recovered by drying in sieves or another suitable drying agent.

Having thus described a few particular embodiments of the invention, it will be apparent to those skilled in the art, in view of the teachings contained herein, that various alterations, modifications, and improvements not specifically described are available and within the scope of the present invention. Such alterations, modifications, and improvements, as are made obvious by this disclosure, are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A process for producing fluorinated organic compounds comprising:
(a) fluorinating in a first fluorination step at least one compound of Formula (I):

$$CHX=CClC(X)_3 \tag{I}$$

with a first fluorinating agent in a first reactor to produce at least one compound of Formula (IA):

$$CHX=CClCF_3 \tag{IA}$$

where each X is independently H or Cl;
(b) fluorinating in a second fluorination step said at least one compound of Formula (IA) in a second reactor to produce at least one compound of Formula (IB):

$$CH_2XCClFCF_3 \tag{IB}$$

with a second fluorinating agent;
(c) recycling at least a portion of said at least one compound of Formula (IB) back to said first reactor as a recycled compound of Formula (IB); and (d) dehydrochlorinating said recycled compound of Formula (IB) in said first reactor to produce at least one compound of Formula (II):

$$CF_3CF=CHZ \tag{II}$$

where Z is independently H or Cl.

2. The process of claim 1 wherein said at least one compound of Formula (I) comprises at least one tetrachloropropene.

3. The process of claim 1 wherein said at least one compound of Formula (I) comprises $CH_2=CClCCl_3$.

4. The process of claim 1 wherein said at least one compound of Formula (I) comprises $CHCl=CClCCl_2H$.

5. The process of claim 1 wherein said at least one compound of Formula (I) is selected from the group consisting of $CH_2=CClCCl_3$, $CHCl=CClCCl_2H$, and combinations of these.

6. The process of claim 1 wherein said at least one compound of Formula (IA) comprises a monochloro-trifluoropropene.

7. The process of claim 1 wherein said at least one compound of Formula (IA) comprises HCFO-1233xf.

8. The process of claim 1 wherein said at least one compound of Formula (IB) comprises a mono-chloro-tetrafluoropropane.

9. The process of claim 1 wherein said at least one compound of Formula (IB) comprises HCFC-244bb.

10. The process of claim 1 wherein said at least one compound of Formula (II) comprises HFO-1234yf.

11. The process of claim 1 wherein said at least one compound of Formula (IA) is HCFO-1233xf, said at least one compound of Formula (IB) is HCFC-244bb, and said at least one compound of Formula (II) is HFO-1234yf.

12. The process of claim 1 wherein said first fluorination step can be carried out batch wise, continuous, or a combination of these.

13. The process of claim 1 wherein said first reactor comprises at least two reactor zones separated by a physical barrier, whereby said first fluorination step is performed in a first reactor zone, and said dehydrochlorination step is performed in a second reactor zone.

14. The process of claim 1 wherein said first fluorinating agent comprises hydrogen fluoride, and wherein said first fluorination step is a gas phase reaction in the presence of at least one fluorination catalyst.

15. The process of claim 1 wherein said second fluorination step is a liquid phase reaction in the presence of at least one fluorination catalyst.

16. The process of claim 1 wherein said second fluorination step is a gas phase reaction in the presence of at least one fluorination catalyst.

17. The process of claim 1 wherein said dehydrochlorination step is a gas phase reaction in the presence of at least one dehydrochlorination catalyst.

18. The process of claim 1 wherein said dehydrochlorination step is performed contemporaneously with said first fluorination step.

19. A process for producing fluorinated organic compounds comprising:
(a) introducing one or more feed streams into a first reactor containing a fluorination catalyst and a dehydrochlorination catalyst, wherein said feed streams collectively comprise hydrogen fluoride, at least one compound of Formula (I):

$$CHX=CClC(X)_3 \tag{I}$$

and at least one compound of Formula (IB):

$$CH_2XCClFCF_3 \quad (IB)$$

where each X is independently H or Cl;
(b) contacting said one or more feed streams with said fluorination catalyst and said dehydrochlorination catalyst to produce a first intermediate product stream comprising at least one compound of Formula (IA):

$$CHX=CClCF_3 \quad (IA)$$

and at least one compound of Formula (II):

$$CF_3CF=CHZ \quad (II)$$

where Z is independently H or Cl;
(c) converting at least a portion of said at least one compound of Formula (IA) into said at least one compound of Formula (IB) in a second reactor to produce a second intermediate product stream;
(d) separating said second intermediate product stream into a product stream rich in said at least one compound of Formula (II) and recycle product stream rich in said at least one compound of Formula (IB);
(e) introducing said recycle product stream into said first reactor as said one or more feed streams.

20. A process for producing tetrafluoropropene comprising:
(a) introducing one or more feed streams into a first reactor containing a fluorination catalyst and a dehydrochlorination catalyst, wherein said feed streams collectively comprise tetrachloropropene, hydrogen fluoride, and HCFC-244bb;
(b) contacting said one or more feed streams with said fluorination catalyst and said dehydrochlorination catalyst to produce a first intermediate product stream comprising HCFO-1233xf and HFO-1234yf;
(c) converting at least a portion of said HCFO-1233xf into HCFC-244bb in a second reactor to produce a second intermediate product stream;
(d) separating said second intermediate product stream into a product stream rich in HFO-1234yf and a recycle product stream rich in HCFC-244bb; and
(e) introducing said recycle product stream into said first reactor as said one or more feed streams.

* * * * *